US007556965B2

(12) United States Patent
Hallek et al.

(10) Patent No.: US 7,556,965 B2
(45) Date of Patent: *Jul. 7, 2009

(54) STRUCTURAL PROTEIN OF ADENO-ASSOCIATED VIRUS WITH MODIFIED ANTIGENICITY, ITS PRODUCTION AND ITS USE

(75) Inventors: Michael Hallek, Cologne (DE); Anne Girod, Jesenwang (DE); Martin Reid, Starnberg (DE)

(73) Assignee: MediGene AG, Planegg/Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/880,592

(22) Filed: Jul. 23, 2007

(65) Prior Publication Data

US 2008/0064081 A1    Mar. 13, 2008

Related U.S. Application Data

(63) Continuation of application No. 10/031,313, filed as application No. PCT/EP00/06692 on Jul. 13, 2000, now Pat. No. 7,252,997.

(30) Foreign Application Priority Data

Jul. 15, 1999   (DE) ............................ 199 33 288

(51) Int. Cl.
C12N 15/00 (2006.01)
(52) U.S. Cl. .................. 435/440; 435/5; 435/69.1; 424/233.1
(58) Field of Classification Search ............ None
See application file for complete search history.

(56) References Cited

U.S. PATENT DOCUMENTS

| 5,276,136 | A | 1/1994 | Skubitz et al. |
| 6,491,907 | B1 | 12/2002 | Rabinowitz et al. |
| 2001/0031463 | A1 | 10/2001 | Kleinschmidt et al. |
| 2002/0192823 | A1 | 12/2002 | Bartlett |

FOREIGN PATENT DOCUMENTS

| WO | WO 95/23867 | 9/1995 |
| WO | WO 96/00587 | 1/1996 |
| WO | WO 97/08298 | 3/1997 |
| WO | WO 97/38723 | 10/1997 |
| WO | WO 99/67393 | 12/1999 |

OTHER PUBLICATIONS

Anderson, "Human Gene Therapy," *Nature* 392:25-30 (1998).
Asokan et al., "AAV Does the Shuffle," *Nature Biotechnology* 24:158-160 (2006).
Buning et al., "Receptor Targeting of Adeno-Associated Virus Vectors," *Gene Therapy* 10:1142-1151 (2003).
Grifman et al., "Incorporation fo Tumor-Targeting Peptides into Recombinant Adeno-Associated Virus Capsids," *Molecular Therapy* 3:964-975 (2001).
Hoque et al., "Nuclear Transport of the Major Capsid Protein is Essential for Adeno-Associated Virus Capsid Formation," *Journal of Virology* 73:7912-7915 (1999).
Huttner et al., "Genetic Modifications of the Adeno-Associated Virus Type 2 Capsid Reduce the Affinity and the Neutralizing Effects of Human Serum Antibodies," *Gene Therapy* 10:2139-2147 (2003).
Kmiec, "Gene Therapy," *American Scientist* 87: 240-247 (1999).
Maass et al., "Recombinant Adeno-Associated Virus for the Generation of Autologous, GeneModified Tumor Vaccines: Evidence for a Hgh Transduction Efficiency into Primary Epithelial Cancer Cells," *Human Gene Therapy* 9:1049-1059 (1998).
Maheshri et al., "Directed Evolution of Adeno-Associated Virus Yields Enhanced Gene Delivery Vectors," *Nature Biotechnology* 24:198-204 (2006).
Marshall, "Second Child in French Trial is Found to Have Leukemia," *Science* 299:320 (2003).
Meng et al., "Tumor Suppressor Genes as Targets for Cancer Gene Therapy," *Gene Therapy of Cancer Chapter* 1, pp. 3-18 (1999).
Mizukami et al., "Adeno-Associated Virus Type 2 Binds to a 150-Kilodalton Cell Membrane Glycoprotein," *Virology* 217:124-130 (1996).
Moskalenko et al., "Epitope Mapping of Human Anti-Adeno-Associated Virus Type 2 Neutralizing Antibodies: Implications for Gene Therapy and Virus Structure," *Journal of Virology* 74:1761-1766 (2000).
Nicklin et al., "Efficient and Selective AAV2-Mediated Gene Transfer Directed to Human Vascular Endothelial Cells," *Molecular Therapy* 4:174-181 (2001).
Perabo et al., "In Vitro Selection of Viral Vectors with Modfied Tropism: The Adeno-Associated Virus Display," *Molecular Therapy* 8:151-157 (2003).
Qing et al., "Human Fibroblast Growth Factor Receptor 1 is a CeReceptor for Infection by Adeno-Associated Virus 2," *Nature Medicine* 5:71-77 (1999).
Ried et al., "Adeno-Associated Virus Capsids Displaying Immunoglobulin-Binding Domains Permit Antibody-Mediated Vector Retargeting to Specific Cell Surface Receptors," *Journal of Virology* 76:4559-4566 (2002).
Russell, "Replicating Vectors for Gene Therapy of Cancer: Rsks, Limitations and Prospects," *European Journal of Cancer* 30A:1165-1171 (1994).
Shi et al., "Insertional Mutagenesis of the Adeno-Associated Virus Type 2 (AAV2) Capsid Gene and Generation of AAV2 Vectors Targeted to Alternative Cell-Surface Receptors," *Human Gene Therapy* 12:1697-1711 (2001).
Shi et al., "RGD Inclusion of Vp3 Provides Adeno-Associated Virus Type 2 (AAV2)-Based Vectors with a Heparan Sulfate-Independent Cell Entry Mechanism," *Molecular Therapy* 7:515-525 (2003).

(Continued)

*Primary Examiner*—Stacy B Chen
(74) *Attorney, Agent, or Firm*—Clark & Elbing LLP

(57) ABSTRACT

The present invention relates to a structural protein of adeno-associated virus (AAV) which comprises at least one modification which brings about a reduction in the antigenicity, its production and use.

8 Claims, No Drawings

OTHER PUBLICATIONS

Smith et al., "The Challenges of genome Sequence Annotation or 'the Devil is in the Details'," *Nature Biotechnology*, 15:1222-1223 (1997).

Spear et al., "Evidence for Two Nucleotide Sequence Orientations Within the Terminal Repetition of Adeno Associated Virus DNA," *Journal of Virology* 24:627-634 (1977).

Starovasnik et al., Structural Mimicry of a Native Protein by a Minimized Binding Domain,*Proc. Natl. Acad. Sci.* USA 94:10080-10085 (1997).

Summerford et al., "Membrane Associated Heparan Sulfate Proteoglycan is a Recepor for Adeno-Associated Virus Type 2 Virions," *Journal of Virology* 72:1438-1445 (1998).

Summerford et al., "α$\beta$5 Integrin: A Co-receptor for Adeno-Associated Virus Type 2 Infection," *Nature Medicine* 5:78-82 (1999).

Tseng et al., "Evolutionary Model fo Predicting Protein Function by Matching Local Surfaces: a Bayesian Monte Carlo Approach," The Ninth Annual Conference on Research in Computational Molecular Biology, May 1418, 2005.

Verma et al., "Gene TherapyPromises, Problems and Prospects," *Nature* 389:239-242 (1977).

Wendtner et al., "Efficient Gene Transfer of CD40 Ligand into Primary BCLL cells using recombinant Adeno-Associated Virus (rAAV) Vectors,"*Blood* 100:1655-1661 (2002).

White et al., "'Designer' Gene Therapy May Target Specific BodyArea," *Business News* 2:1-2 (2003).

White et al., "Targeted Gene Delivery to Vascular Tissue in Vivo by TropismModified Adeno-Associated Virus Vectors," *Curculation* 109:513-519 (2004).

Wobus et al., "Monoclonal Antibodies Against the Adeno-Associated Virus Type 2 (AAV-2) Capsid: Epitope Mapping and Identification of Capsid Domains Involved in AAV-2-Cell Interaction and Neutralization of AVV-2 Infection," *Journal of Virology* 74:9281-9293 (2000).

Wu et al., "Mutational Analysis of the Adeno-Associated Virus Type 2 (AAV2) Capsid Gene and Construction of AAV2 Vectors with Altered Tropism," *Journal of Virology* 74:8635-8647 (2000).

Aumailley et al., "Identification of the ArgGly-Asp Sequence in Laminin A Chain as a Latent CellBinding Site Being Exposed in Fragment P1," *FEBS* 262:82-86 (1990).

Bartlett et al., "Targeted Adeno-Associated Virus Vector Transduction of Nonpermissive Cells Mediated by a Bispecific F (ab'$_F$)$_2$ Antibody," *Nature Biotechnology* 17:181-186 (1999).

Chapman et al., "Structure, Sequence, and Function Correlations Among Parvoviruses,"*Virology* 194:491-508 (1993).

Chiorini et al., "High-Efficiency Transfer of the T Cell Co-Stimulatory Molecular B7-2 to Lymphoid Cells Using High-Titer Recombinant Adeno-Associated Virus Vectors," *Human Gene Therapy* 6:1531-1541 (1995).

Cosset et al., "Targeting Retrovirus Entry,"*Gene Therapy* 3:946-956 (1996).

Douglas et al., "Targeted Gene Delivery by TropismModified Adenoviral Vectors," *Nature Biotechnology* 14:1574-1578 (1996).

Girod et al. "Genetic Capsid Modifications Allow Efficient ReTargeting of Adeno-Associated Virus Type 2," *Nature Medicine* 5:1052-1056 (1999).

Hermonat et al., "Genetics of Adeno-Associated Virus: Isolation and Preliminary Characterization of Adene Associated Virus Type 2 Mutants," *Journal of Virology* 51:329-339 (1984).

Luo et al., "Preliminary X-Ray Crystallographic Analysis of Canine Parovirus Crystals," *J. Mol. Biol.* 200:209-211 (1988).

Kotin, "Prospects for the Use of Adeno-Associated Virus as a Vector For Human Gene Therapy," *Human Gene Therapy* 5:793-801 (1994).

Krasnykh et al., "Generation of Recombinant Adenovirus Vectors With Modified Fibers for Altering Viral Tropism," *Journal of Virology* 70:6839-6846 (1996).

Muzyczka, "Use of Adeno-Associated Virus as a General Transduction Vector for Mammalian Cells," *Current Topics in Microbiology and Immunology*158:97-129 (1992).

Nimako et al., "Human Papillomavirus-Specific Cytotoxic T Lymphocytes in Patients with Cervical Intraepithelial Neoplasia Grade III," *Cancer Research* 57:4855-4861 (1997).

Ohno et al., "Cell-Specific Targeting of Sindbis Virus Vectors Displaying IgGBinding Domains of Protein A," *Nature Biotechnology* 15:763-767 (1997).

Ruffing et al., "Mutations in the Carboxy Terminus of Adeno-Associated Virus 2 Capsid Proteins Affect Viral Infectivity: Lack of an RGD Integrin-Binding Motif," *Journal of General Virology* 75:3385-3392 (1994).

Ruffing et al., "Assembly of Viruslike Particles by Reombinant Structural Proteins of Adeno-Associated Virus Type 2 in Insect Cells," *Journal of Virology* 66:6922-6930 (1992).

Rutledge et al., "Infectious Clones and Vectors Derived from Adeno-Associated Virus (AAV) Serotypes Other Than AAV Type 2," *Journal of Virology* 72:309-319 (1998).

Steinbach et al., "Assembly of Adeno-Associated Virus Type 2 Capsids in vitro,"*Journal of General Virology* 78:1453-1462 (1997) (Abstract).

Stevenson et al., "Selective Targeting Human Cells by a Chimeric Adenovirus Vectr Containing a Modified Fiber Protein," *Journal or Virology* 71:4782-4790 (1997).

Srivastava et al., "Nucleotide Sequence and Organization of the AdeneAssociated Virus 2 Genome," *Journal of Virology* 45:555-564 (1983).

Tarpey et al., "Human Cytotoxic TLymphocytes Stimulated by Endogenously Processed Human Papillomavirus Type 11 E7 Recognize a Peptide Containing a HLAA2 (A*0201) Motif,"*Immunology* 81:222-227 (1984).

Tsao et al., "The Three-Dimensional Structure of Canine Parvovirus and Its Functionallmplications," *Science* 251:1456-1464 (1991).

Valsesia-Wittmann et al., Modifications in the Binding Domain of Avian Retrovirus Envelope Protein to Redirect the Host Range of Retorviral Vectors, *Journal of Virology*68:4609-4619 (1994).

Wickham et al., "Increased In Vitro and In Vivo Gene Transfer by Adenovirus Vectors Containing Chimeric Fiber Proteins," *Journal of Virology* 71:8221-8229 (1997).

Wistuba et al., "Subcellular Compartmentalization of Adeno-Associated Virus Type 2 Assembly,"*Journal of Virology* 71:1341-1352 (1997).

Wistuba et al., "Intermediates of Adeno-Associated Virus Type 2 Assembly: Identification of Soluble Complexes Containing Rep and Cap Proteins," *Journal of Virology*69:5311-5319 (1995).

Wu et al., "The Canine Parvovirus Empty Capsid Structure,"*J. Mol. Biol.* 233:231-244 (1993).

Yang et al., "Development of Novel Cell Surface CD34Targeted Recombinant Adenoassociated Virus Vectors for Gene Therapy," *Human Gene Therapy* 9:1929-1937 (1998).

STRUCTURAL PROTEIN OF ADENO-ASSOCIATED VIRUS WITH MODIFIED ANTIGENICITY, ITS PRODUCTION AND ITS USE

CROSS REFERENCE TO RELATED APPLICATIONS

This application is a continuation of U.S. application Ser. No. 10/031,313, filed Jun. 3, 2002, which is the U.S. National Stage of International Application No. PCT/EP2000/06692, filed Jul. 13, 2000, which claims benefit of German patent application 19933288.6, filed Jul. 15, 1999.

The present invention relates to a structural protein of adeno-associated virus (AAV) which comprises at least one modification which brings about a reduction in the antigenicity, its production and use.

The AAV virus belongs to the family of parvoviruses. These are distinguished by an icosahedral, non-enveloped capsid which has a diameter of 18 to 30 nm and which contains a linear, single-stranded DNA of about 5 kb. Efficient replication of AAV requires coinfection of the host cell with helper viruses, for example with adenoviruses, herpesviruses or vaccinia viruses. In the absence of a helper virus, AAV enters a latent state, the viral genome being capable of stable integration into the host cell genome. The property of AAV integrating into the host genome makes it particularly interesting as a transduction vector for mammalian cells. In general, the two inverted terminal repeats (ITR) which are about 145 bp long are sufficient for the vector functions. They carry the "cis" signals necessary for replication, packaging and integration into the host cell genome. For packaging in recombinant vector particles, a helper plasmid which carries the genes for nonstructural proteins (Rep proteins) and for structural proteins (Cap proteins) is transfected into cells suitable for packaging, for example HeLa or 293 cells, which are then infected, for example, with adenovirus. A lysate containing recombinant AAV particles is obtained after some days. Suitable helper plasmids are described, for example, by Chiorini et al., (1995) Hum. Gene Ther. 6, 1531-1541 or Girod et al. (1999), Nat. Med.

The AAV capsid consists of three different proteins: VP1, VP2 and VP3, whose relative proportions are 5% VP1, 5% VP2 and 90% VP3. The AAV capsid genes are located at the right-hand end of the AAV genome and are encoded by overlapping sequences of the same open reading frame (ORF) using different start codons and two differently spliced variants of a transcript. The VP1 gene contains the whole VP2 gene sequence, which in turn contains the whole VP3 gene sequence with a specific N-terminal region. The fact that the overlapping reading frames code for all three AAV capsid proteins is responsible for the obligatory expression of all capsid proteins, although to different extents.

The molecular masses of the capsid proteins are 87 kD for VP1, 73 kD for VP2 and 62 kD for VP3. The sequences of the capsid genes are described, for example, in Srivastava, A. et al. (1983), J. Virol., 45, 555-564; Muzyczka, N. (1992), Curr. Top. Micro. Immunol., 158, 97-129, Ruffing, N. et al. (1992), J. Virol., 66, 6922-6930 or Rutledge, E. A. et al. (1998) J. Virol. 72, 309-319. The physical and genetic map of the AAV genome is described, for example, in Kotin, R. M. (1994), Human Gene Therapy, 5, 793-801.

Also known are various AAV serotypes, of which the human AAV serotype 2 (AAV2) has been most thoroughly researched. These analyses have shown that AAV viruses have advantageous properties as viral vectors for somatic gene therapy. The essential advantages are the lack of pathogenicity for humans, the stable integration of viral DNA into the cellular genome, the ability to infect non-dividing cells, the stability of the virion, which makes purification to high titers ($10^{13}$ to $10^{14}$ particles per ml) possible, the relatively low immunogenicity, and the absence of viral genes and gene products in the recombinant AAV vector, which is advantageous from the viewpoint of safety for use in gene therapy. The cloning of genes into the AAV vector now takes place by methods generally known to the skilled person, as described, for example, in WO 95/23 867, in Chiorini J. A. et al. (1995), Human Gene Therapy, 6, 1531-1541 or in Kotin, R. M. (1994), supra.

The use in particular of viral vectors in gene therapy is greatly dependent on the antigenicity of the system used because a high antigenicity is associated with an enhanced immune response which might interfere with the result of the therapy. The antigenicity of the AAV virus is therefore also of crucial importance for its utilizability in therapy. The term antigen means substances which, after introduction into the human or animal body, induce a specific immune response. This is manifested either by the production of antibodies (humoral immune response) and development of a cell-mediated immunity (cellular immune response) or by a specific immunological tolerance. The general prerequisite for an immune response (for the immunogenicity of the antigen) is that the antigen is recognized by the body as foreign, that it has an MW of >1 kDa and belongs to the class of proteins or polysaccharides, less commonly deoxyribonucleic acids or lipids. Complex structures such as, for example, bacteria, viruses or erythrocytes (particulate antigens) are generally even more effective antigens, that is to say have high antigenicity. Antigenicity therefore means for the purpose of this invention the ability to interact (be recognized) with the immune system (humoral and cellular) by binding. The term moreover encompasses the immunogenicity, that is to say also the ability to induce an immune response. It is moreover possible in principle in particular with viruses for antigenic structures for antibody binding to be determined not only by the primary structure but also by the secondary, tertiary or quaternary structure of the capsid proteins or capsids.

Chapman M. S. and Rossmann M. G. (1993), Virology, 194, 491-508 were able to identify the principal antigenic determinants of the CPV capsid by sequence comparisons with various parvoviruses from which the antigenic differences between the capsid proteins were predicted. According to this study, the antigenicity of the CPV capsid protein is linked primarily to externally exposed loops with high sequence variability. On the other hand, no such studies have yet been carried out on the AAV virus capsid. Only WO 96/00587 describes AAV capsid fusion proteins in which, for example, the DNA coding for a clinically relevant antigen is inserted into the DNA coding for a capsid protein without interfering with capsid formation, and the construct is expressed as AAV capsid fusion protein. The clinically relevant antigens are epitopes which derive, for example, from bacteria (e.g. *salmonella*), viruses (e.g. env-HIV) or tumor cells. The resulting AAV capsid fusion proteins are intended to produce an immune response, that is to say ensure increased antigenicity of the AAV viruses.

A reduced antigenicity of AAV is not suggested in the prior art. However, for practical use of AAV vectors—particularly in gene therapy—a reduced antigenicity compared with the wild type or with AAV vectors derived from the wild type is advantageous. This is because wild type AAV certainly also has antigenic determinants. Thus, there are anti-AAV2 Ig-positive individuals for whom therapy with AAV vectors of a wild-type antigenicity is inevitably difficult or impossible.

Likewise, a patient might on repeated treatment with AAV vectors increasingly develop a humoral and/or cellular immune response to the AAV vectors used. Such an immunization would make a therapy less successful or unsuccessful. Thus, a lower antigenicity of a recombinant AAV virus or a greater difference between its antigenicity and a wild-type virus or a previously used recombinant AAV virus means that its therapeutic use appears more promising.

It was therefore an object of the present invention to reduce the antigenicity of the AAV virus in particular of a structural protein compared with the wild type. It was particularly intended to develop by modification AAV vectors which make specific and efficient gene transfer possible but avoid the immune response better or completely. The modification ought therefore preferably to be such that at the same time there is a negligible reduction or at least a retention of the infectivity of the virus.

It has now been found, surprisingly, that structural or capsid proteins of AAV can be modified in such as way that this brings about a reduction in the antigenicity with a negligible reduction in the infectivity, which is at least retained.

One aspect of the present invention is therefore a structural protein of AAV which comprises at least one modification which brings about a reduction in the antigenicity.

The reduction in the antigenicity means for the purpose of the invention and the above definitions the reduction in the antibody production and/or antibody binding through modification, deletion or addition of particular sequences or epitopes or a combination of these measures, especially in particular epitopes and sequences present in the wild type. A reduced antigenicity means, for example, a reduced immunization of an organism through a therapy with an AAV vector. In this connection, an antigenicity which is merely modified in absolute terms, i.e. in the average strength of the immune response, is also to be regarded as reduced for the purpose of this invention if the structural protein of the invention does not induce an antibody (immune) response which would have been induced by the wild type. Such an antigenicity which has been merely been modified in absolute terms may lead to a reduced immunization if AAV vectors of the invention differing in antigenicity are employed in successive treatments. The modified antigenicity may moreover relate both to the humoral and to the cellular immune response.

For the humoral immune response, the reduced antigenicity can be detected, for example, through an antibody which is able to bind to the unmodified (wild-type) AAV capsid protein or AAV capsid no longer recognizing, or recognizing considerably less well, the modified AAV capsid protein or AAV capsid of the invention. Such detections can be carried out by standard methods such as an enzyme-linked immunoabsorbent assay (ELISA). A suitable antibody is, for example, the A20 monoclonal antibody (see Wistuba, A. et al. (1997) J. Virol., 71, 1341-52), which specifically recognizes only completely assembled AAV2 capsids of the wild type, but no free capsid proteins.

For the cellular immune response, the modified antigenicity can be detected through AAV-specific immune cells not being so strongly stimulated by antigen-presenting cells which have been infected with particles of modified structural proteins as by antigen-presenting cells which have been infected with particles of original structural proteins. This method is in analogy to the methods for vaccinia- and adenoviruses (Tarpey, I. et al., (1994), Immunology, 81, 222-7; Nimako, M. et al., (1997), Cancer Res. 57, 4855-61). Stimulation of immune cells can be measured quantitatively for example by a cytokine assay (Chapter 6.2 to 6.24 in Current Protocols in Immunology (1999), edited by Coligan J. E. et al., John Wiley & Sons).

It is particularly preferred for the modification in the structural protein of the invention to bring about a negligible reduction in the infectivity of the virus or for the infectivity to be at least retained. Infectivity means for the purpose of this invention the ability to transduce cells.

In addition, the structural protein of the invention preferably continues to be capable of particle formation, i.e. of formation of an icosahedral capsid, in particular in the form of an AAV capsid, because particles and capsids are particularly suitable as carriers of selected compounds, e.g. rAAV transduction vectors. The formation of particles can be detected, for example, by electron microscopy. Another detection is the sedimentation behavior during a cesium chloride density gradient centrifugation with subsequent, optional, detection of viral DNA present in the particles.

In general, the modification may be present in the VP1, VP2 and/or VP3 structural protein, with preference for the VP1 and/or the VP3 structural protein. The structural protein may moreover be derived from all AAV serotypes, in particular from human serotypes, preferably from AAV1, AAV2, AAV3, AAV4, AAV5 and/or AAV6, especially from AAV2, AAV3 and/or AAV6.

The modification(s) is/are preferably located on the virus surface. For determining the surface-located regions of the structural proteins, it was surprisingly found according to the present invention that CPV (canine parvovirus) and AAV2 sequences and structures are comparable. It is therefore possible to have recourse preferably to known crystal structures of parvoviruses such as of parvovirus B19 or of CPV and to identify, with the aid of homology comparisons, protein domains which are located on the virus surface. According to the present invention, therefore, for example a computer-assisted comparison between CPV and AAV2, and parvovirus B19 and AAV2, has surprisingly led reproducibly to the identification of loops in VP3, whose sequence varies, i.e. which have a low homology and which are expected to be located on the virus surface. Since the antigens for the humoral immune response must be accessible for antibodies and therefore on the virus surface, these loops represent preferred candidates for modifications. Thus, the known crystal structure of the CPV VP2 capsid protein (for example Luo M. (1988), J. Mol. Biol., 200, 209-211; Wu and Rossmann (1993), J. Mol. Biol., 233, 231-244; Tsao J. et al. (1991) Science, 251, 1456-1464) was taken as pattern, because of the great similarity to AAV2 VP3 in the secondary structure of the protein, in order to find the regions which are exposed on the viral capsid surface and, because of the local amino acid sequence, are sufficiently flexible to withstand insertion of a peptide sequence, for example. In this case, care was taken that no secondary structural elements of the AAV2 capsid protein which would destabilize the capsid were selected.

In a preferred embodiment, the modification(s) are located at the N terminus of the structural protein, because it has been found that, for example, in the case of parvovirus B19 the N terminus is located on the cell surface.

Another possibility for determining the surface-located regions of the structural proteins is to compare the nucleic acid sequences coding for the capsids from different AAV serotypes. It is possible to use for this purpose, for example, known DNA sequences from different AAV serotypes, such as AAV1, AAV2, AAV3, AAV4, AAV5 or AAV6, for structural analyses of possible capsid morphologies of, for example, AAV2, it being possible ab initio to calculate possible tertiary structures and assign sequence regions on the basis of generally known amino acid properties to the inner or outer capsid regions. It was thus possible, for example, according to the present invention to establish possible insertion sites in the VP3 region of the AAV2 capsid, and these made it possible to insert, for example, peptides and express them on the viral surface (see below).

A modification means, for example, a modification of the capsid proteins which is achieved by covalent or noncovalent linkage of a molecule to one or more amino acids or amino acid sequences. Thus, a capsid protein can be modified, for example, by covalent linkage of mono- or oligosaccharides, biotin or other high molecular weight compounds to one or more amino acids. The modification may, however, also be achieved by covalent linkage of low molecular weight compounds such as a hydroxyl group to one or more amino acids. A further possibility is for molecules or molecule complexes to be attached to the capsid proteins via noncovalent linkage, and thus shield antigenic regions. This may be, for example, the antigen binding site of immunoglobulins, e.g. an $F_{ab}$ fragment or other molecules which have high affinity for the antigenic region or adjacent regions. Molecules of these types can be screened for their affinity for example from molecule libraries. If the three-dimensional structure of the antigenic region or of the capsid protein is known, it is possible to design and synthesize a number of potentially binding molecules which can then be tested for their affinity.

However, modification also means, for example, one or more mutations, that is to say changes in the sequence of the amino acids. The term mutation encompasses, for example, a point mutation, a mutation of more than one amino acid, one or more deletion(s), one or more insertion(s) or a combination of these mutations. It is moreover possible for the point mutation or the mutation of more than one amino acid to be present within T or B cell epitopes and for the modification simultaneously to consist of point mutations, mutations of more than one amino acid, insertions and/or deletions.

In a preferred embodiment there is insertion of protein or peptide, preferably immunosuppressive protein or peptide. The peptide in this case can consist of, for example, 5 to 30 amino acids, preferably 8 to 20 amino acids and, in particular, 10 to 18 amino acids. The peptide has, for example, the sequence QAGTFALRGDNPQG (SEQ ID NO: 1) or a sequence which is highly homologous therewith.

A structural protein of the invention which is particularly preferred comprises at least one other modification. By this is meant that the structural protein comprises in addition to a modification which brings about a reduction in the antigenicity of the virus also another modification which does not necessarily also bring about a reduction in the antigenicity of the virus. Particular preference is given in this connection to another modification which brings about an alteration, preferably increase, in the infectivity of the virus.

In a further preferred embodiment, the further modification/s represent/s one or more deletions and/or one or more insertions in the structural protein or combinations of these modifications. The insertion in this connection is preferably the insertion of a cell membrane receptor ligand, of a Rep protein or peptide, for example in the form of a Rep domain, of an immunosuppressive protein or peptide and/or of a protein or peptide with a signal for double strand synthesis of a transgene or foreign gene.

Examples of further insertions are, inter alia, integrins, cytokines or receptor binding domains of cytokines, integrins or growth factors such as, for example, GM-CSF, IL-2, IL-12, CD40L, TNF, NGF, PDGF or EGF, single-chain antibodies binding to cell surface receptors, so-called single chain antibodies (scFv), for example single-chain antibodies binding to the surface receptors CD40, CD40L, B7, CD28 or CD34, or epitopes or receptor binding sites which are, for example, in turn recognized by particular antibodies, for example anti-CD40L monoclonal antibodies or by chemical substances or hormones, for example catecholamines.

In a preferred embodiment of the other modification there is insertion of antibody-binding structures such as, for example, protein A, protein G or anti-Fc antibodies or parts thereof. To these are coupled in turn specific antibodies against particular cell surface structures (for example against CD40 in the case of lymphatic cells or against CD34 in the case of hematopoietic cells).

In a preferred embodiment, the modification(s) is(are) brought about by one or more insertions at the XhoI cleavage site of the VP1-encoding nucleic acid and in another preferred embodiment at the BsrBI cleavage site of the VP1-encoding nucleic acid. A further preferred embodiment of the structural protein of the invention is brought about by a deletion between the BsrBI/HindII cleavage sites of the VP1-encoding nucleic acid and one or more insertions, preferably at the deletion site.

In a further preferred embodiment of the present invention, the modification(s) is(are) brought about by one or more deletions between the XhoI/XhoI cleavage sites of the VP1-encoding nucleic acid, which comprises 62 amino acids (Hermonat, P. L. et al. (1984), J. Virol., 51, 329-339). In a further preferred and corresponding embodiment, the deletion(s) is/are located between the BsrBI/HindII cleavage sites of the VP1-encoding nucleic acid, which is located within the deletion described above and comprises 29 amino acids. This deletion has the advantage that it has no overlap with the Rep gene and therefore has essentially no effect on the packaging mechanism.

In a further preferred embodiment, one or more insertions are present in the VP3 structural protein (Rutledge, E. A. et al. (1998) supra) before and/or after at least one amino acid in the sequence selected from YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT (SEQ ID NO: 6), EQYGS (SEQ ID NO: 7), LQRGN RQAAT (SEQ ID NO: 9), NVDFT VDTNG (SEQ ID NO: 9), because these sites are located on the exposed sites of a loop, in which case the risk of changing the VP3 structure is low.

The point mutation(s), the mutation(s) of several amino acids, the deletion(s) or insertion(s) is/are carried out by generally known methods by deletion and insertion in the gene coding for the structural protein. The deletions can be introduced into the individual structural protein genes for example by PCR-assisted mutagenesis. The insertions can be introduced by generally known methods, for example by hydrolysis by restriction endonucleases of the appropriate structural protein genes and subsequent ligase reaction. Subsequent expression of the mutated gene leads to the structural protein of the invention.

Another aspect of the present invention is also a structural protein of the invention in the form of an AAV particle, in particular in the form of an AAV capsid, because particles and capsids are particularly suitable as carriers of selected compounds, for example rAAV transduction vectors.

Further aspects of the present invention are a nucleic acid, preferably an RNA or DNA, in particular a double-stranded DNA, coding for a structural protein of the invention.

The present invention also relates to a cell, preferably a mammalian cell, for example a COS cell, HeLa cell or 293 cell, comprising a nucleic acid of the invention. Cells of this type are suitable, for example, for preparing the recombinant AAV particles.

A further aspect of the present invention is therefore also a process for producing a structural protein of the invention, in particular for producing a structural protein according to the invention in the form of an AAV particle, where a suitable cell comprising a nucleic acid coding for the structural protein according to the invention is cultivated and, where appropriate, the expressed structural protein is isolated. For example, the structural protein of the invention can be isolated on a cesium chloride gradient as described, for example, in Chiorini, J. A. et al. (1995), supra.

Another aspect of the present invention also relates to a pharmaceutical comprising a structural protein of the invention or a nucleic acid of the invention or a cell of the invention and, where appropriate, suitable excipients and additives such as, for example, a physiological saline solution, stabilizers, proteinase inhibitors, DNAse inhibitors etc.

A further aspect of the present invention is a pharmaceutical which comprises at least two different structural proteins of the invention, each of which has different modifications. It is particularly preferred in this connection that they differ in antigenicity.

A further preferred aspect is a kit comprising at least two different structural proteins of the invention, in which each structural protein is present in the kit separate from the other structural protein(s).

For use of the kit or of the pharmaceutical having at least two different structural proteins of the invention, for example as part of a therapy, initially one structural protein is used. Structural proteins differing in antigenicity is/are used for one or more subsequent application(s). Therapy using the pharmaceutical or kit thus encompasses successive administration of structural proteins of the invention. The pharmaceutical and kit thus have the advantage that (1) the potentiation, induced on repeated use of the same structural protein, of an immune response can be avoided and that (2) in the event of induction of an immune response during the first use, through use of a structural protein differing in antigenicity the defence response against this second use proves to be less effective than against a use with the first structural protein. The immunization of the patient which is reduced in this way increases the efficacy. For continued applications it is thus possible for there to be multiple alternation between different structural proteins in order thus to minimize the immunization of a patient. A set of a plurality of structural proteins in the form of infectious particles differing in antigenicity is preferred, these being used as vector for the multiple transfer of, for example, identical therapeutic genes. Another pharmaceutical comprises a set of structural proteins in the form of infectious particles which are used as vector for different therapies.

A further aspect of the present invention relates to the use of the structural protein of the invention for altering the antigenicity of AAV, for transforming a cell and/or—in the form of suitable rAAV vectors—for gene therapy. Gene therapy means a type of therapy in which, through introduction of nucleic acids into cells, an effector gene and thus usually a protein is expressed. A distinction is made in principle between in vitro and in vivo methods. In in vitro methods, cells are removed from the organism and tranduced ex vivo with vectors in order subsequently to be introduced again into the same or into another organism. For in vivo gene therapy, vectors, for example for controlling tumors, are administered systemically (e.g. via the blood stream) or locally (e.g. into the tumor).

A considerable advantage of the present invention is that the antigenicity can be altered essentially without loss of the packaging efficiency of recombinant AAV vectors—and thus of the basic prerequisite for infectivity—inside the capsid of the virus through the mutagenesis according to the invention of AAV structural proteins. The present invention is therefore especially suitable for in vivo transduction of cells, for example for somatic gene therapy, if reduced immunization of patients is desired.

The following examples are intended to illustrate the invention in detail without restricting it.

EXAMPLE 1

P1 Mutation in VP3

The starting point was a plasmid pUC-AV2 which was produced by subcloning the 4.8 kb BglII fragment of pAV2 (ATCC 37261, ref. 53) into the BamHI cleavage site of pUC19 (New England BioLabs Inc.). Mutations were carried out at defined sites in the plasmid by means of the PCR-assisted mutagenesis known to the skilled worker. This involved insertion of a sequence coding for P1, a 14 AA peptide with the AA sequence QAGTFALRGDNPQG, which contains the RGD binding motif of a laminin fragment (Aumailly et al. (1990) FEBS Lett. 262, 82-86), after nucleotides 2985, 3345 and 3963. This corresponds to an insertion after amino acids 261, 381 and 587 in the AAV2 capsid protein (named according to the number of amino acids (AA) counted after the AA from the start of the N terminus in VP-1 of AAV2). In the subsequent PCR, in each case 2 mutation-specific primers are used, and a plasmid, pcap, which contains only the cap gene and is formed by cutting the 2.2 kb EcoRI-BspMI fragment out of pUC-AV2 and inserting it into the EcoRI cleavage site of pUC19, is used as template. The PCR products are subsequently amplified in bacteria and sequenced, and the 1.4 kb EcoNI-XcmI fragment which contains P1 is subcloned in pUC-AV2 in which the corresponding wild-type cap sequence has been cut out. Consequently, the plasmids (mutants) which are named after the AA insertion sites pI-261, pI-381 and pI-587 contained the complete AAV2 genome. The correspondingly mutated proteins are referred to as I-261, I-381 and I-587.

EXAMPLE 2

Production of AAV2 Particles

HeLa cells (a human cervical epithelial cell line) were transfected with the plasmids of example 1, incubated for about 20 h and then infected with adenovirus type 5. 72 h after the infection, the cells were disrupted and the AAV2 particles were purified on a CsCl gradient.

EXAMPLE 3

Characterization of the Capsid Mutants of Example 1

The intention of these experiments was to establish whether the capsid mutants are able to package the viral genome and form complete capsids. AAV2 particles of the mutants of example 2 were examined to find whether and, if so, how many particles carry the viral genome and how much DNA was packaged in the capsid mutants. For this purpose, the virus particles (mutants and wild type) purified in example 2 were treated with DNAse, blotted and hybridized with a Rep probe.

The titer which emerged from this showed no quantitative or qualitative difference from the wild type (see table 1). The viruses retained the ability to package the genome.

It was further possible to confirm by electron microscopic analysis that the capsid is also formed.

The mutations were therefore not carried out in regions which are important for correct folding, capsid assembly or packaging of the genome. The function of the AAV particles of the invention is unimpaired.

EXAMPLE 4

Antigenicity of the Capsid Mutants of Example 1

In order to be able to ensure the antigenicity of the mutated capsids, A20 monoclonal antibodies (A20MAb) were employed in an ELISA in a further experiment. A20MAb reacts specifically with the completely assembled AAV2 capsid of the wild type (Wistuba et al., (1997), J. Virol. 71, 1341-1352). Once again, the results are shown in table 1. It emerges from this that the A20 monoclonal antibodies no longer able to bind owing to the insertion in the mutants I-261 and I-381, in contrast to the wild type and I-587.

TABLE 1

Packaging efficiency and antigenicity of the virus mutants produced in example 1

| Virus stock | Genomic virus titer | ELISA with A20 MAb |
|---|---|---|
| Wild-type capsid Mutants | $8 \cdot 10^{13}$ | $6 \cdot 10^{12}$ |
| I-261 | $1 \cdot 10^{12}$ | n.m. |
| I-381 | $1 \cdot 10^{12}$ | n.m. |
| I-587 | $4 \cdot 10^{13}$ | $3 \cdot 10^{12}$ |

The genomic virus titers (dot-blot) and the titer with A20 capsid ELISA are shown. The concentrations are stated in particles/ml. "n.m." means "not measurable".

EXAMPLE 5

Infection Tests with Capsid Mutants of Example 1

In order to test the tropism of the capsid mutants I-261, I-381 and I-587, cells of the cell line Co-115 were infected with the mutated viruses. Co-115 cells were used to test the wild-type receptor tropism of the virions because the latter can be transduced with wild-type AAV2. Three days after the infection, the cells were investigated by immunofluorescence measurement using an anti-Rep antibody to find whether the viral Rep protein is expressed (Wistuba et al. (1997) J. Virol. 71, 1341-1352; Wistuba et al. (1995) J. Virol. 69, 5311-5319). Cells were grown to 70% confluence on microscope slides and incubated with various concentrations of viral preparations of the invention in serum-free medium together with adenovirus 5. The titers of the viral preparations were determined three days later by in situ detection of Rep protein synthesis in an immunofluorescence assay (Rep titer). The immunofluorescence staining was carried out in this case with AAV2-infected cells by a method of Wistuba et al. (Wistuba et al. (1997) J. Virol. 71, 1341-1352; Wistuba et al. (1995) J. Virol. 69, 5311-5319). The microscope slides were washed once with PBS, fixed in methanol (5 min, 4° C.) and then treated with acetone (5 min, 4° C.). The cells were then incubated with the monoclonal antibodies 76-3, which reacts with Rep proteins of AAV2, at room temperature for one hour. This was followed by washing and incubation with a rhodamine-conjugated anti-mouse secondary antibody at a dilution of 1:50 in PBS with 1% BSA for one hour. The titers were calculated from the last limiting dilution of the viral stock solution which led to fluorescence-positive cells.

Rep-positive CO115 cells were detectable after infection with wild-type AAV2 and the mutants I-261 and I-587, the infectivity of the mutants being two to three orders of magnitude less than that of the wild type, and one mutant was not infectious (I-381) (table 2). However, it was possible to show that the infectivity was retained for mutant I-261 despite reduced antigenicity (see example 4).

TABLE 2

Virus titer on the cell surface

| Virus stock | Titer on CO115 cells |
|---|---|
| Wild-type capsid Mutants | $2 \cdot 10^{9}$ |
| I-261 | $7 \cdot 10^{6}$ |
| I-381 | n.m. |
| I-587 | $1 \cdot 10^{7}$ |

The titers for the wild type-susceptible CO115 cells are shown. The titers are expressed in Rep EFU/ml for I-261, I-381 and I-587 as for the wild type. EFU here means expression-forming units (expressing forming unit). Moreover "n.m." means "not measurable".

The invention claimed is:

1. A method for reducing the antigenicity, relative to wild-type AAV, of an AAV capsid, the method comprising introducing at least one modification into a structural protein of AAV, the structural protein being selected from the group consisting of AAV VP1, VP2, and VP3, wherein the modification brings about a reduction in the antigenicity of the capsid, relative to wild-type AAV and wherein the modified structural protein forms capsids, and wherein the modification(s) is/are located directly adjacent to at least one amino acid in a sequence selected from the group consisting of YKQIS SQSGA (SEQ ID NO: 2), YLTLN NGSQA (SEQ ID NO: 3), YYLSR TNTPS (SEQ ID NO: 4), EEKFF PQSGV (SEQ ID NO: 5), NPVAT EQYGS (SEQ ID NOS: 6, 7), LQRGN RQAAT (SEQ ID NO: 8), and NVDFT VDTNG (SEQ ID NO: 9).

2. The method as claimed in claim 1, wherein at least one of said modifications is based on a covalent or noncovalent linkage to the structural protein of one or more compound(s) selected from the group consisting of biotin, a mono- or oligosaccharide, a hydroxide group, and a $F_{ab}$ fragment, and one or more amino acid(s) or amino acid sequence(s).

3. The method as claimed in claim 1, wherein the modification is a mutation selected from the group consisting of a point mutation, a mutation of more than one amino acid, one or more deletion(s), one or more insertion(s), and a combination of these mutations.

4. The method as claimed in claim 1, wherein the modification comprises a protein or a peptide inserted into the structural protein.

5. The method as claimed in claim 4, wherein the inserted protein or peptide is selected from the group consisting of a cell membrane receptor ligand, a Rep protein or peptide, an integrin, a cytokine or receptor binding domain of a cytokine, a growth factor, a single-chain antibody, a single-chain antibody binding to a cell surface receptor, a catecholamine, protein A or a part thereof, protein G or a part thereof, and an anti-Fc antibody or a part thereof.

6. The method as claimed in claim 1, wherein the structural protein comprises at least one other modification.

7. The method as claimed in claim 1, wherein at least one of the modifications is/are located directly adjacent to at least one amino acid in the sequence LQRGN RQAAT (SEQ ID NO: 8).

8. The method as claimed in claim 1, wherein at least one of the modifications is/are located directly adjacent to at least one amino acid in the sequence NVDFT VDTNG (SEQ ID NO: 9).

* * * * *

SEQUENCE LISTING

<160> NUMBER OF SEQ ID NOS: 9

<210> SEQ ID NO 1
<211> LENGTH: 14
<212> TYPE: PRT
<213> ORGANISM: Mus musculus

<400> SEQUENCE: 1

Gln Ala Gly Thr Phe Ala Leu Arg Gly Asp Asn Pro Gln Gly
1               5                   10

<210> SEQ ID NO 2
<211> LENGTH: 10
<212> TYPE: PRT
<213> ORGANISM: Adeno-Associated Virus

<400> SEQUENCE: 2

Tyr Lys Gln Ile Ser Ser Gln Ser Gly Ala

```
                    1               5                   10

<210> SEQ ID NO 3
<211> LENGTH: 10
<212> TYPE: PRT
<213> ORGANISM: Adeno-associated Virus

<400> SEQUENCE: 3

Tyr Leu Thr Leu Asn Asn Gly Ser Gln Ala
1               5                   10

<210> SEQ ID NO 4
<211> LENGTH: 10
<212> TYPE: PRT
<213> ORGANISM: Adeno-Associated Virus

<400> SEQUENCE: 4

Tyr Tyr Leu Ser Arg Thr Asn Thr Pro Ser
1               5                   10

<210> SEQ ID NO 5
<211> LENGTH: 10
<212> TYPE: PRT
<213> ORGANISM: Adeno-associated virus

<400> SEQUENCE: 5

Glu Glu Lys Phe Phe Pro Gln Ser Gly Val
1               5                   10

<210> SEQ ID NO 6
<211> LENGTH: 5
<212> TYPE: PRT
<213> ORGANISM: Adeno-associated virus

<400> SEQUENCE: 6

Asn Pro Val Ala Thr
1               5

<210> SEQ ID NO 7
<211> LENGTH: 5
<212> TYPE: PRT
<213> ORGANISM: Adeno-associated virus

<400> SEQUENCE: 7

Glu Gln Tyr Gly Ser
1               5

<210> SEQ ID NO 8
<211> LENGTH: 10
<212> TYPE: PRT
<213> ORGANISM: Adeno-associated virus

<400> SEQUENCE: 8

Leu Gln Arg Gly Asn Arg Gln Ala Ala Thr
1               5                   10

<210> SEQ ID NO 9
<211> LENGTH: 10
<212> TYPE: PRT
<213> ORGANISM: Adeno-associated virus

<400> SEQUENCE: 9

Asn Val Asp Phe Thr Val Asp Thr Asn Gly
1               5                   10
```